(12) United States Patent
Glasser et al.

(10) Patent No.: US 9,320,645 B2
(45) Date of Patent: Apr. 26, 2016

(54) APPROACH TO ADMINISTERING OCULAR MEDICATION

(71) Applicants: Terry Glasser, Houston, TX (US); Spencer Obie, Houston, TX (US)

(72) Inventors: Terry Glasser, Houston, TX (US); Spencer Obie, Houston, TX (US)

( * ) Notice: Subject to any disclaimer, the term of this patent is extended or adjusted under 35 U.S.C. 154(b) by 0 days.

(21) Appl. No.: 13/904,197

(22) Filed: May 29, 2013

(65) Prior Publication Data

US 2014/0358124 A1  Dec. 4, 2014

(51) Int. Cl.
  *A61L 31/16*  (2006.01)
  *A61P 27/02*  (2006.01)
  *A61F 9/00*  (2006.01)

(52) U.S. Cl.
  CPC .................................... *A61F 9/0008* (2013.01)

(58) Field of Classification Search
  CPC .......................... A61M 2210/0612; A61F 9/17
  See application file for complete search history.

(56) References Cited

U.S. PATENT DOCUMENTS

| | | | |
|---|---|---|---|
| 2,722,216 A | 11/1955 | Robbins | |
| 3,058,466 A | 10/1962 | Routsong | |
| 3,075,527 A | 1/1963 | Bechtold | |
| 3,826,258 A | 7/1974 | Abraham | |
| 3,828,777 A | 8/1974 | Ness | |
| 3,911,098 A | 10/1975 | Capozza | |
| 4,036,230 A * | 7/1977 | Adams | 604/294 |
| 4,540,408 A * | 9/1985 | Lloyd | 604/294 |
| 4,778,457 A | 10/1988 | York | |
| 5,147,337 A | 9/1992 | Plone | |
| 5,314,419 A | 5/1994 | Pelling | |
| 5,467,147 A | 11/1995 | Feranda | |
| 5,928,662 A | 7/1999 | Phillips | |
| 6,090,086 A | 7/2000 | Bolden | |
| 6,595,940 B1 * | 7/2003 | D'Alessio et al. | 604/3 |
| 6,728,573 B1 | 4/2004 | Beck et al. | |
| 7,780,976 B2 | 8/2010 | Van Dalen | |
| 2004/0106906 A1 | 6/2004 | Yaacobi | |
| 2005/0143817 A1 * | 6/2005 | Hunter | A61B 17/11 623/11.11 |
| 2005/0182351 A1 * | 8/2005 | Henley et al. | 604/20 |
| 2009/0170770 A1 * | 7/2009 | Hafezi-Moghadam | 514/12 |
| 2009/0196903 A1 * | 8/2009 | Kliman | 424/423 |
| 2010/0226997 A1 | 9/2010 | Bowman et al. | |
| 2012/0251409 A1 | 10/2012 | Hrboticka | |

FOREIGN PATENT DOCUMENTS

| | | |
|---|---|---|
| EP | 1 332 754 | 6/2003 |
| EP | 1 407 732 | 4/2004 |

OTHER PUBLICATIONS

Thomson, S. and Cleland, J. Quain's Elements of Anatomy. 1867. p. 708. See attached.*

* cited by examiner

*Primary Examiner* — Tatyana Zalukaeva
*Assistant Examiner* — Sara Sass
(74) *Attorney, Agent, or Firm* — Brian F. Russell; Russell Ng PLLC (57) ABSTRACT

The invention is a device and a method for delivering a dose of a pharmaceutical agent to the eye. The device and method provide a safe and effective way to instill a specified dose of the agent to the eye virtually independent of gravity and posture. The device includes a filter matrix in which the fluid capture and release properties can be modified. The filter matrix is attached to a flexible handle with an impermeable or semipermeable membrane there between.

17 Claims, 13 Drawing Sheets

3 – Dimensional Representation of the Filter Matrix Applicator: Disciform

Enlarged View of Filter

3 – Dimensional Representation of the Filter Matrix Applicator

Fig. 1

Enlarged View of Filter

Fig. 1A

3 – Dimensional Representation of the Filter Matrix Applicator

Fig. 2

3 – Dimensional Representation of the Filter Matrix Applicator: Disciform

Enlarged View of Filter

3 – Dimensional Representation of the Filter Matrix Applicator: Disciform

Fig. 4

3 – Dimensional Representation of the Solid-State Carrier Matrix Filter Matrix Applicator

Enlarged View of Solid-State Carrier Filter Matrix

3 – Dimensional Representation of the Solid-State Carrier Matrix Filter Matrix Applicator

Fig. 6

3 – Dimensional Representation of FMA Being Removed From Sleeve And
Medication Applied to Untreated Filter Matrix Applicator

3 – Dimensional Representation of Filter Matrix Applicator with the Handle Acting as the Barrier Membrane

Fig. 8

3 – Dimensional Representation of the Use of a Filter Matrix Applicator Being Applied to the Lower Fornix

APPROACH TO ADMINISTERING OCULAR MEDICATION

BACKGROUND

This invention relates to a process and a device for adding a controlled dose of fluid to the eye. Conventional eye drops are difficult to use even for experienced patients. They are more problematic for children, the elderly, patients with impaired motor skills, and caregivers. Patients risk improper dosing, contamination of the eye dropper container, expensive waste due to spillage, and injury to the eyes from contact with the dropper bottle. These factors contribute to poor compliance. In addition, preservatives are added to the drops to provide medicine stability and reduce microbial contamination. These preservatives are known to cause morphological changes to the cornea, conjunctiva, and surrounding areas, which lead to irritation, stinging, burning, epiphora, hyperemia, keratitis, allergic and immune response, and scarring (1).

Subsequent reflex tearing leads to dilution of the medication, which can further alter pharmacodynamics. The quantity and concentration of the drug from conventional eye drops must be increased in order to account for the decreased bioavailability due to reflex tearing and the biophysiologic dynamics of the eye's structure. At least 80% of the drop is lost from excess tearing, spillage due to overflow from the eye's cul de sac, and rapid drainage through the nasolacrimal duct which increases the risk of systemic side effects (2). The eye has a tear turnover rate of 16% per minute which doubles after using conventional eye drops (3). In order to reach the aqueous humor at measurable levels, high concentrations of a drug are needed for one drop to be effective since only 3% of conventional eye drops penetrate the cornea (4).

New delivery systems include solutions, suspensions, sprays, gels, inserts, emulsions, mucoadhesives, collagen shields, and contact lenses. These are in addition to devices designed to facilitate the instillation of a drop to the eye. Although these methods are relatively safe, they have not fully addressed the main problems associated with drop delivery. In addition, they have not been implemented on a large scale (5).

What is needed is a new method and device that overcomes the basic challenges of the current eye dropper system which are:
1. Gravity.
2. Reduced bioavailability due to reflex tearing, eye drop spillover, and eye drop splash-back.
3. Difficult physical manipulation of the eye dropper bottle system by patients and caregivers.
4. Psychological apprehension of the eye drop instillation process.
5. Eye drop preservation process.

SUMMARY OF THE INVENTION

The subject invention provides a new method for applying a controlled dose of most any ophthalmic agent to the eye without an eyedropper. The device of the present invention comprises a filter matrix attached to an elongated flexible handle separated by a barrier membrane. With the present invention, the medication is impregnated within the filter matrix of the filter matrix applicator (FMA) through various methods and ready for activation at a later desired date.

The applicator facilitates the easy instillation of a fully medicated dose of controlled, precise concentration to provide an expected pharmaceutical effect.

Each medicated applicator can contain a single dose of medication within the filter matrix as intended for its own pharmaceutical intent. The medication would be impregnated into the sterile filter matrix, which can be designed with modifiable levels of absorption and saturation according to the pharmacodynamics or chemical properties of the drug being delivered. The length, width, and depth of the filter matrix along with the type of interwoven material determine the absorption and saturation level of the filter matrix.

The device and method of the present system is designed to provide an optimal ocular drug delivery, which increases compliance by patients and effectiveness of delivery of the pharmaceutical agent. The present invention further achieves the following objectives:

Objective 1: Making instillation easy, fast, and comfortable for the patient, clinician, or caregiver.

Objective 2: Increasing bioavailability and optimizing contact time while maintaining or improving effective dosing.

Objective 3: Decreasing or eliminating the use of preservatives while maintaining pH balance; thereby reducing side effects.

Objective 4: Decreasing the dilution and drainage caused by excess tearing, spillage, and splash-back.

Objective 5: Decreasing the risk of contamination and injury to the eye by eliminating the dropper bottle modality.

Objective 6: Improving handling and transport (6).

Figure 7:
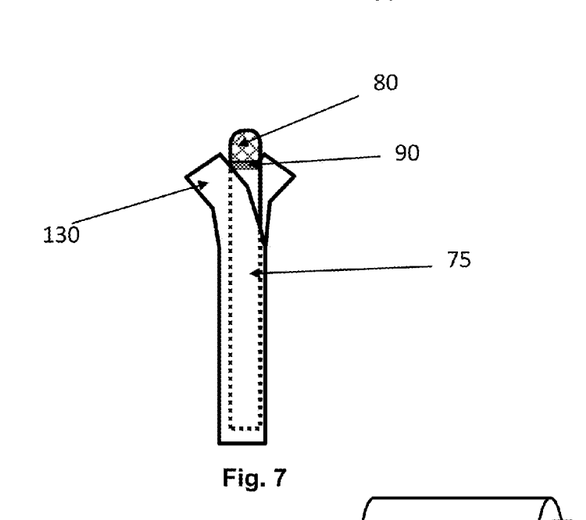
FIG. 7 illustrates the FMA inside a protective sleeve.
Figure 7A:
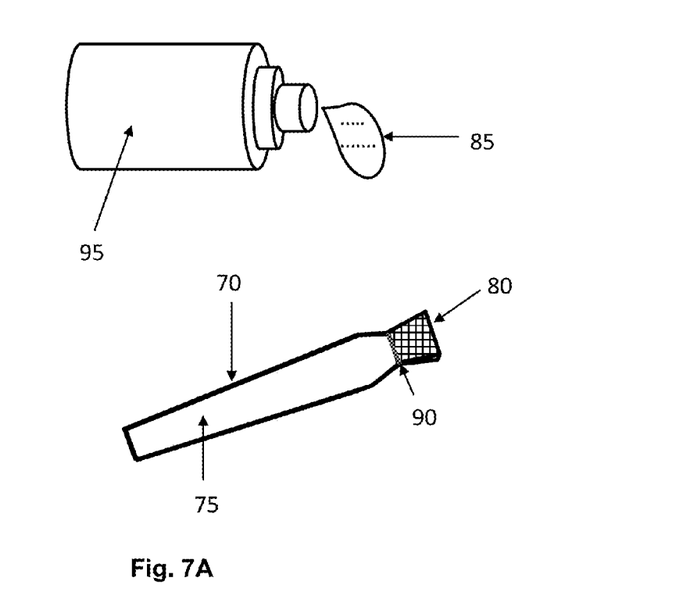
FIG. 7A illustrates an un-medicated FMA used as an applicator for ophthalmic agents from an eye dropper bottle
Figure 8:
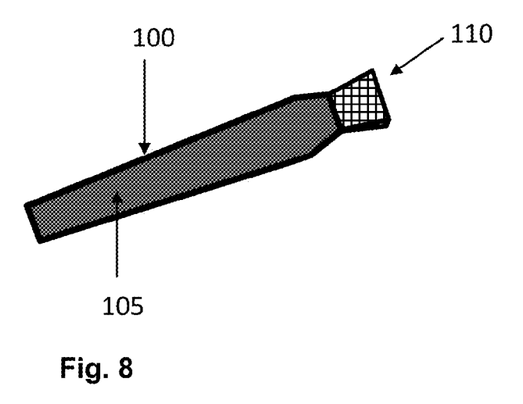
FIG. 8 illustrates the FMA with a handle which behaves as both the barrier membrane and the handle.

DESCRIPTION OF THE PREFERRED EMBODIMENTS

Referring to FIGS. 1, 1A, and 2, the present invention comprises a device, a filter matrix applicator (FMA) (10) comprising a flexible elongated handle (15) bonded to a sterile filter matrix (20), which can be medicated or un-medicated, separated by a barrier membrane (30). Flexible elongated handle (15) of a length of approximately but not limited to 2 inches, with a thickness of at least 0.004 inches. It can be made of paper, plastic or another suitable flexible material. The width of the handle can be 0.25 of an inch.

The barrier membrane (30, 90) can be made of a semi-permeable or impermeable material such as rubber, plastic, waxes, petroleum base product, or another material that is waterproof. As shown in FIG. 7A, once the medicated fluid is placed upon the filter matrix (80), the barrier membrane (90) traps the fluid within the structure of the filter matrix (80) thereby providing a more exact dose of ophthalmic agent to be instilled to the eye. If a pre-medicated FMA (10,32) is used, as shown in FIGS. 1,2,3, and 4, saline which is a non-irritant solution instead of a medicated fluid (95) is applied to the FMA prior to instillation to the eye as shown in FIG. 9. With the present invention any non-irritant eye solution can be use.

In one embodiment, as shown in FIGS. 1 and 1A, the barrier membrane (30) extends the width of the top end of elongated handle (15) and forms a barrier thereto. In an alternative embodiment in FIG. 3, the filter matrix (40) is in the form of a disc and the barrier membrane (52) forms the base at one end of handle (35). As depicted in FIGS. 3 and 3A, filter matrix (40) is bonded to base (52) of handle (35) to form FMA (32).

Referring to FIG. 8, there is shown an alternative embodiment of FMA (100) wherein the handle (105) forms the barrier membrane. In alternative embodiment illustrated in FIG. 8, the barrier membrane serves as both the handle (105) and the waterproof impermeable or semi-permeable membrane. In this embodiment barrier membrane extends the full length and width of the handle (105) and bonds to the filter matrix (110).

As shown in FIGS. 1, 2, and 3, the filter matrix (20, 40) is separated from the handle by a semi-impermeable or impermeable waterproof barrier-membrane (30,52) provides the mechanism wherein the FMA (10) facilitates the efficient and effective entrapment and release of medication into solution for the end-user. In use, the barrier membrane (30, 52) optimizes the amount of medication captured within the FMA (10,32) and precipitated into the resultant drop that is instilled to the eye. The system and device (10) of the present invention reduces the amount of medication that is absorbed or lost in the elongated handle in the prior art without a barrier membrane.

In the present invention, as depicted in FIGS. 1, 2, 3 and 3A, the filter matrix (20, 40) can comprise a plurality of strands or fibers interwoven to create a size that can vary to optimize the capture and release of the ocular agent being used. Interwoven fibers (20, 40) form the matrix to capture the granules of the medicated ocular agent therein. The size of the filter matrix (20) can be ⅜ inches in depth to facilitate a surface area for saturation of the ocular agent within the matrix. The perimeter of the filter matrix (20) in FIG. 1 can be a total of 1 inch. Alternatively the diameter of the filter matrix (40) in FIG. 3 can be 0.25 of an inch in diameter. As shown in FIG. 9, the filter matrix is insoluble and remains intact after instillation of the solution into the conjunctiva of the eye.

However, the shape of the filter matrix (20, 40) can vary in size and shape to aid in efficient instillation of the ocular agent to the eye. In the illustrated embodiment in FIG. 1, the filter matrix (20) depicts a polygonal shape and in FIG. 3, the filter matrix (40) is depicted having a circular shape. However, the shape of the filter matrix (20, 40) is not limited to either shape; instead the shape can vary to optimize the capture and release of the ocular agent. The filter matrix (40) depicted in FIGS. 3 and 1 can be circular, oval, elliptical, or polygonal.

In the present invention, each medicated FMA (10) depicted in FIG. 1 can contain one prescribed medicated dose for a patient. The medication would be impregnated within the FMA (10) in a sterile environment. The fiber can be of various materials with variable levels of absorption and saturation. In use, the more water repellant the strands the lower the saturation level of the filter matrix and the more water absorbent the strands the higher the saturation level of the filter matrix. The strands of the filter matrix can be absorbent such as cotton or less absorbent such as plastic. In the present invention, the strands of the FMA can be made of cotton, rayon, silk, nylon, various plastic fibers, synthetic fibers and/or any other suitable material. The filter matrix can be made of a blend of fibers to adjust the capture and release properties of the FMA (10).

In FIGS. 1 and 3, the semi-flexible handle (15, 35), which is separated from the filter matrix (20, 40) by the impermeable membrane (30, 50) allows for easy placement of the fluid to the eye. The handle can be constructed in various shapes and sizes and of various materials to aid in easy instillation of an ophthalmic agent and to further facilitate proper drop formation to be applied to the matrix.

In an alternative embodiment illustrated in FIGS. 5 and 5A, the volume of the medication is stabilized within an inert semi-permeable carrier (55) made of materials similar to, but not limited to polyvinyl methylcellulose, loosely bound in place to the elongated handle (60) by an inert viscous carrier such as mineral oil or petrolatum or similar compounds (55). The solid-state filter matrix (65) shape can be flat or columnar. The filter matrix (65) size is based on the nature and quantity of active ingredient of the medication. This embodiment reduces the need for a drop to be stabilized on the FMA (62) and also allows for time-release of an ophthalmic compound.

An additional embodiment of the FMA is un-medicated (70), as shown in FIG. 7. In this embodiment, the FMA can be used by placing one drop of ocular medication from an eye dropper bottle onto the FMA and applying directly to the eye in the fashion described in FIG. 9. Therefore, medications not available in a prepackaged FMA form can be administered with the advantages of this new technology.

Creation of the FMA

Once the FMA (10, 32) is manufactured as shown in FIGS. 1, 2, and 3, the filter matrix (20, 40) can be either non-medicated or pharmaceutically impregnated under aseptic conditions. The process of impregnation of filter matrix (20, 40) can occur under aseptic conditions in one of a variety of ways enumerated below:

1) absorbing the medication into the filter matrix in liquid form followed by the removal of the liquid by evaporation within 72 hours;

2) pulverizing the powdered or crystallized form of the medication into the filter matrix;

3) freeze drying the medication into the filter matrix; or 4) stabilizing the volume of medication within an inert viscous carrier/semi-permeable barrier as depicted in the filter matrix in FIG. 7.

Figure 1:
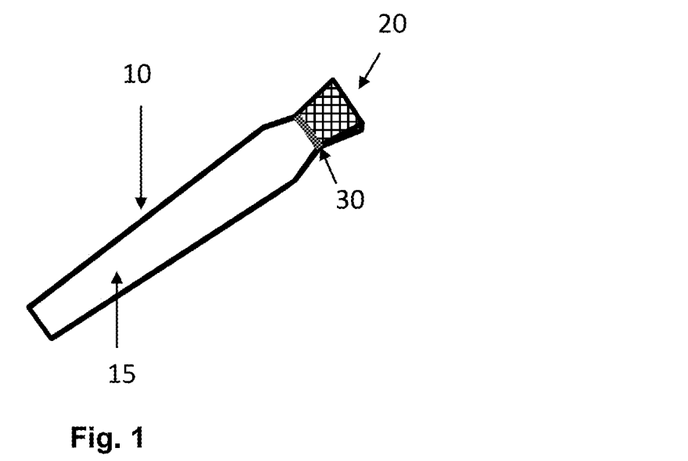
FIG. 1 illustrates a top perspective view of an embodiment of the filter matrix applicator (FMA).
Figure 1A:
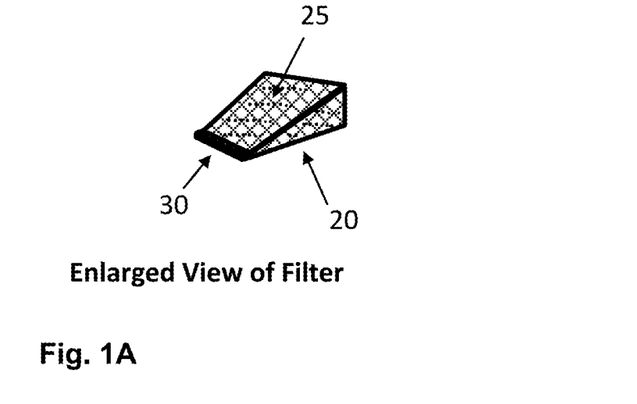
FIG. 1A illustrates a cut away view of an embodiment of the filter matrix.
Figure 2:
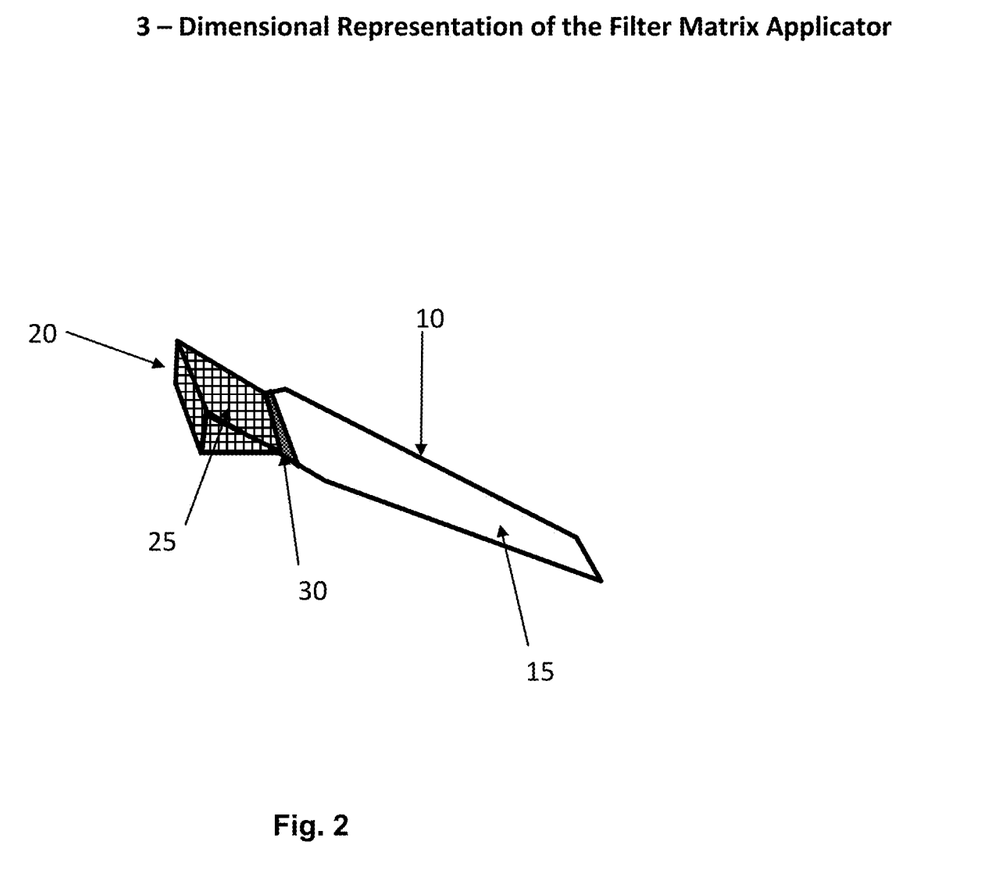
FIG. 2 illustrates the front perspective view of an embodiment of the FMA.
Figure 3:
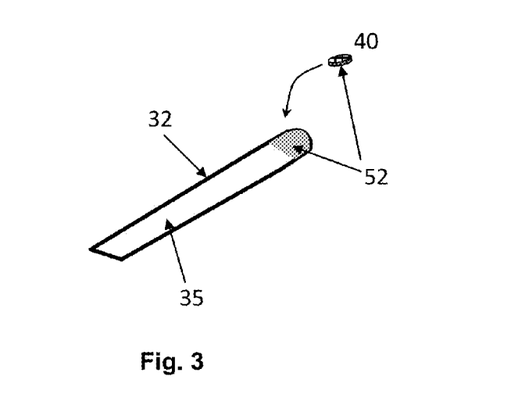
FIG. 3 illustrates an alternative disc form embodiment of the FMA before the treated disk is installed.
Figure 3A:
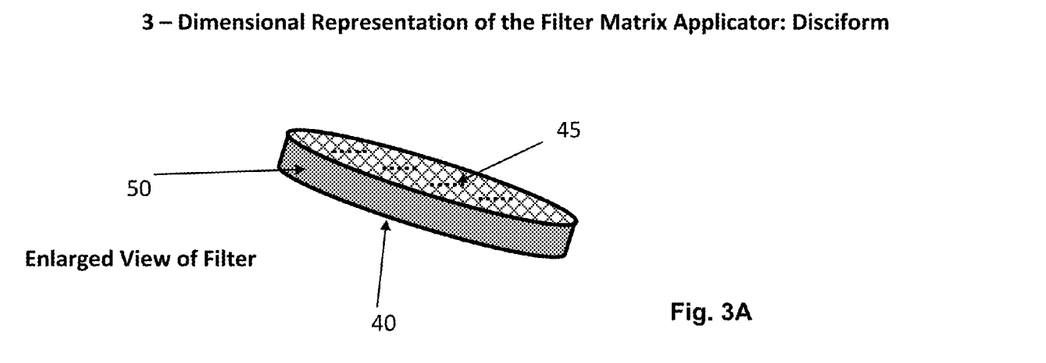
FIG. 3A illustrates a cutaway view of the treated disk of the alternative embodiment of the FMA.
Figure 4:
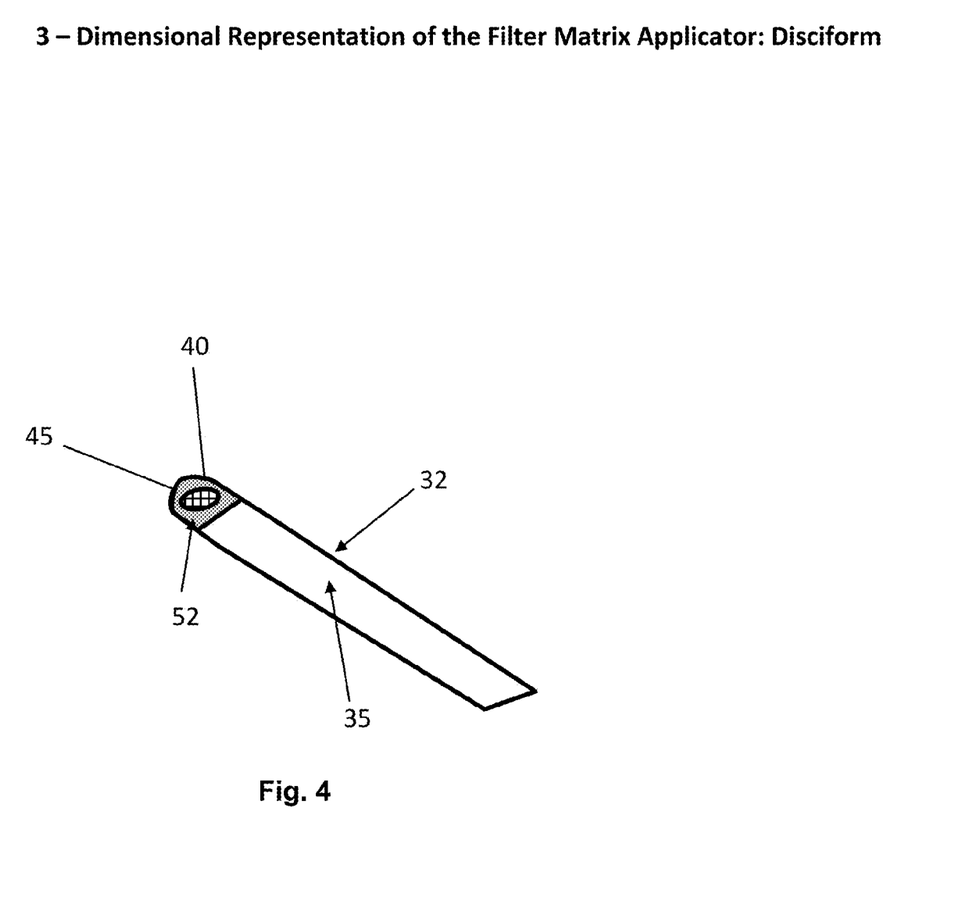
FIG. 4 illustrates the bonded disk in the alternative disc form embodiment of the FMA.
Figure 9:
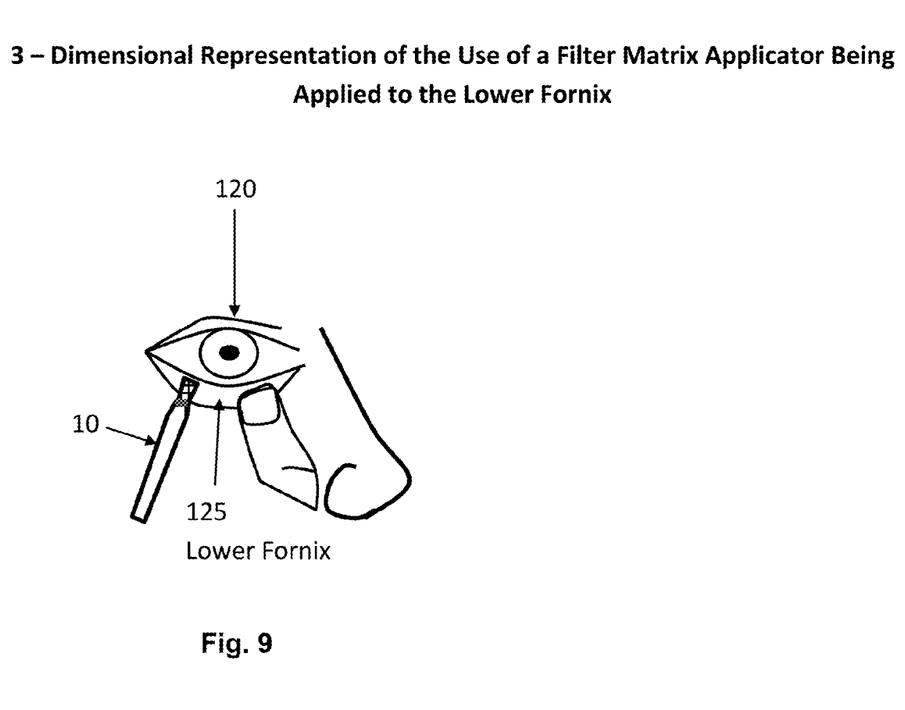
FIG. 9 illustrates the administration of an ophthalmic agent using the FMA by pulling down the lower lid and applying to the conjunctiva.

As depicted in 1, 2, 3, 3A, 4, and 5, once the medicated FMA (10, 32, 62) is prepared under sterile conditions, it can be then individually aseptically packaged and sealed in a sterilized sleeve as depicted in FIG. 7 which can be made of paper, plastic or another suitable material. This medicated filter matrix applicator system of the present invention in FIGS. 1, 3, and 5 facilitates instilling ophthalmic agents in various head positions and body posture, virtually independent of gravity. FIG. 9 illustrates the administration of an ocular compound to the eye using the present invention FMA (10) depicted in FIG. 1.

Operational Method

Figure 5:
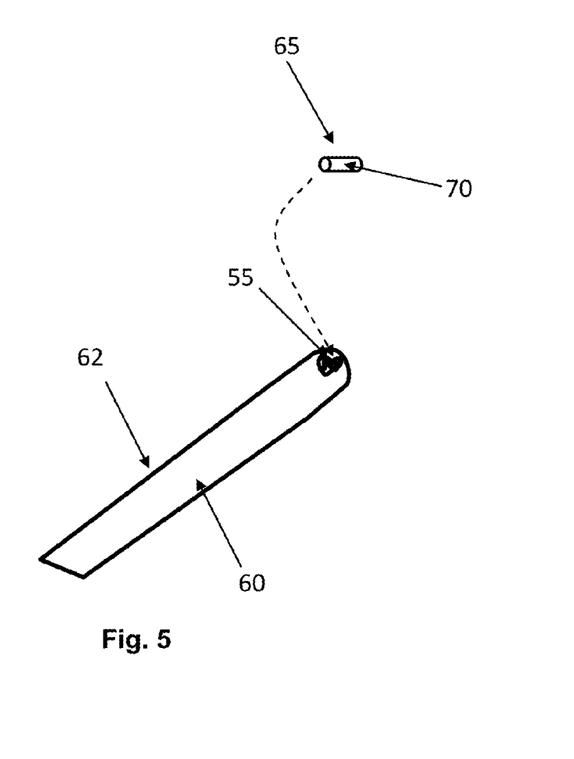
FIG. 5 illustrates an alternative embodiment of the FMA with an un-bonded solid-state carrier.
Figure 5A:
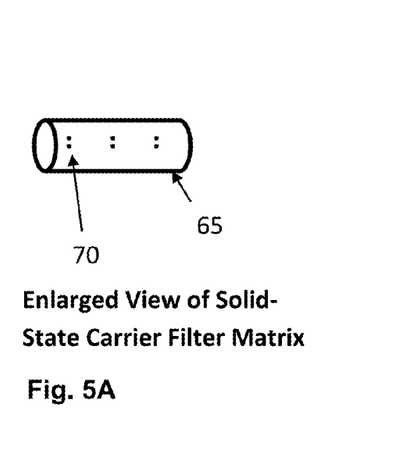
FIG. 5A illustrates a view of the solid-state carrier for the FMA.
Figure 6:
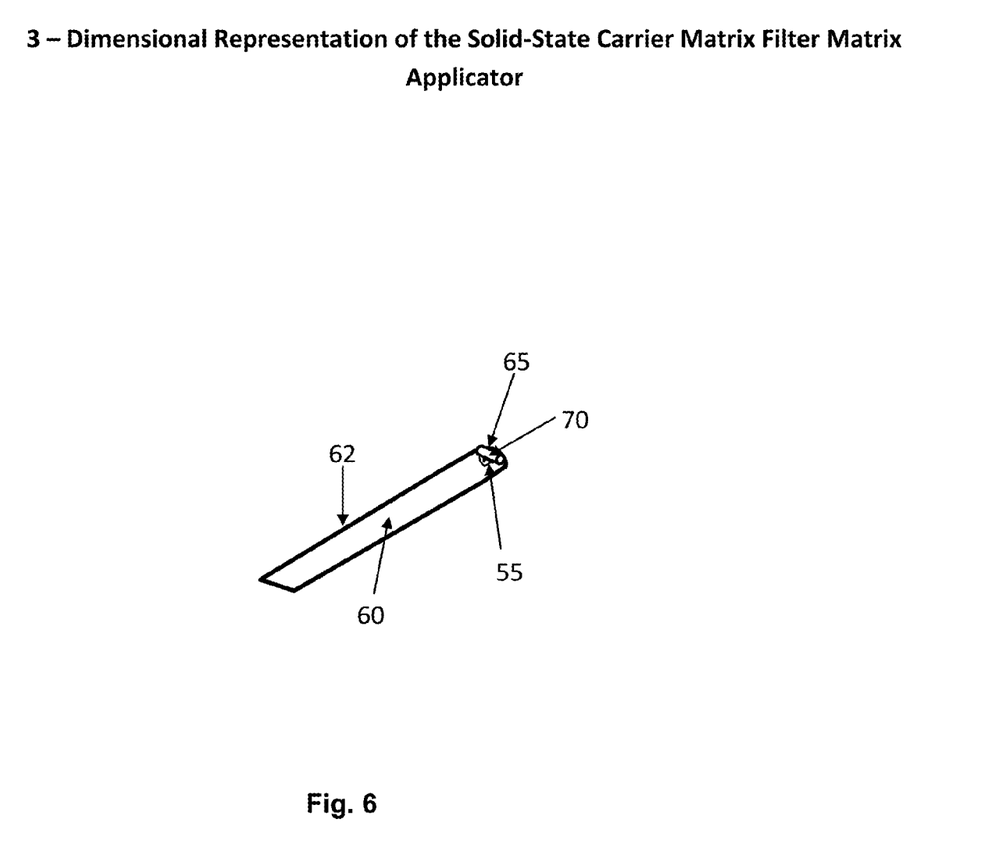
FIG. 6 illustrates the solid-state carrier bonded to form the FMA.

In use, the medicated filter matrix applicator is removed from the sterilized sleeve (FIG. 7) and a drop of sterile saline is placed upon the filter matrix. In the case of FIG. 5, the medicated FMA is simply removed from the protective sleeve and is ready for application without activation from sterile saline. The lower lid of the eye is then pulled down to expose the conjunctiva of the eye and the FMA is directly applied thereto (FIG. 9). The pharmaceutically active solution then is released from the FMA to the eye via capillary action (which describes how a liquid can move against the forces of gravity), the forces of covalent bonding, and Van der Waal forces which determine the attraction of particles in a solution at different temperatures). This method of drug delivery would allow for the entrapment and effective release of medication for easy instillation of a dose of medicine to an eye nearly independent of gravity, less dependent on dexterity, with reduced spillage and overflow, and the possibility of fewer or no preservatives.

In the case of FIG. 5, the semi-permeable component of the FMA (65) is slowly dissolved after being released from the inert viscous carrier. Furthermore, direct corneal and conjunctival absorption is able to be optimized because of reduced reflex tearing, drop spillage, and drop splash back, as is the case in all FMA embodiments (10, 32, 62, 70, 100). Alternatively, a dry medicated FMA (10, 32, 62) can be held in the lower fornix to enable the natural and reflex tears to extract the medication from the filter matrix.

This method of ophthalmic agent delivery is easy to use, safe, sanitary, comfortable, and effective. It greatly reduces the physical and psychological difficulties associated with eye drop instillation via standard eye dropper bottles and tubes. The medicated FMA has a vast range of applications ranging from personal use for eye medicine instillation for patients, to instillation of ocular agents by caregivers in a private or institutional setting, to the application of diagnostic ocular agents for practitioners, even to the instillation of ocular agents and pharmaceuticals in a veterinary setting. Patient, caregiver, and health care practitioner preference will result in significantly improved compliance and reduced side effects.

Experiments

Figure 10:
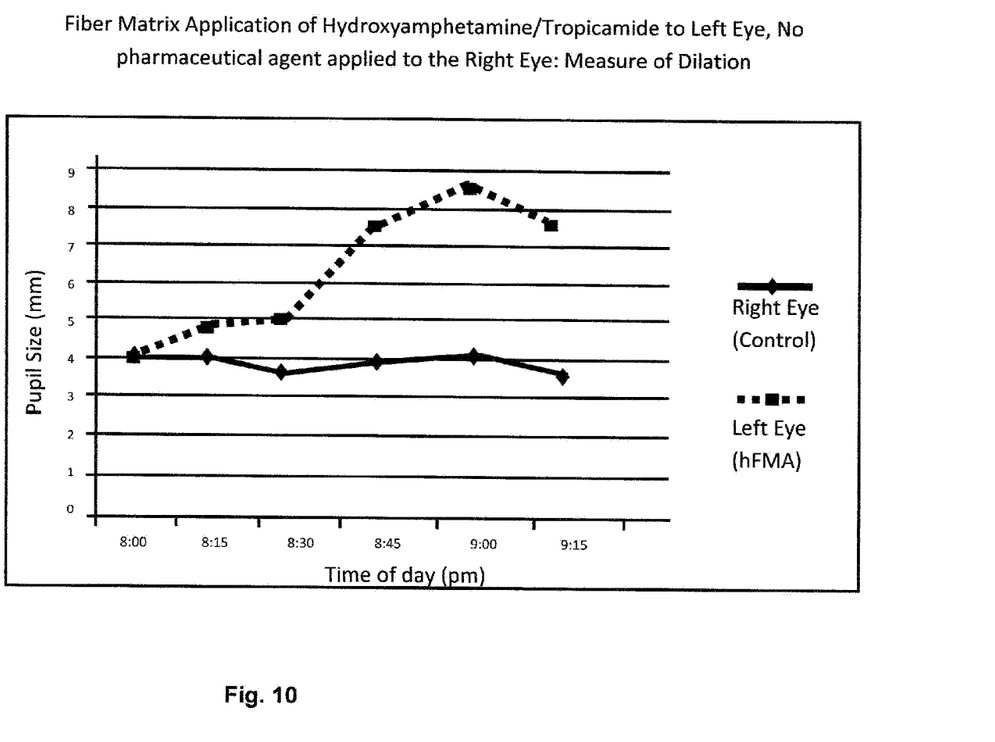
FIG. 10 illustrates the experiment using a mydriatic treated FMA to demonstrate dilation.

Referring to FIG. 10-13, there are shown several experiments conducted by the applicant to show the ease of use and efficacy of the device. Referring to FIG. 10, there is shown an experiment measuring the level of dilation using hydroxyamphetamine/tropicamide. In this experiment, the filter matrix applicator (FMA) was impregnated with approximately ⅓ of a drop of hydroxyamphetamine/tropicamide. Then the FMA was air-dried at room temperature over a 72 hour period. To activate the FMA, a drop of saline solution was applied to the FMA and the FMA was subsequently applied to the left eye. Measurements were observed under normal room lighting. As depicted, it was noted that upon application of the hydroxyamphetamine/tropicamide—FMA (hFMA) to the left eye while leaving the right eye as an untreated control, the subject experienced a substantial and effectively sustained dilation in the left eye. The hFMA was easily self-applied in less than 2 seconds using a mirror. There was no report of burning upon instillation (as is usually noted with standard hydroxyamphetamine/tropicamide eye dropper bottle instillation). However, gradual onset of low grade burning was noted within 1 minute of application (although significantly less and of shorter duration than with hydroxyamphetamine/tropicamide in eye drop form from an eye dropper bottle). The subject was a 35 year old male.

Figure 11:
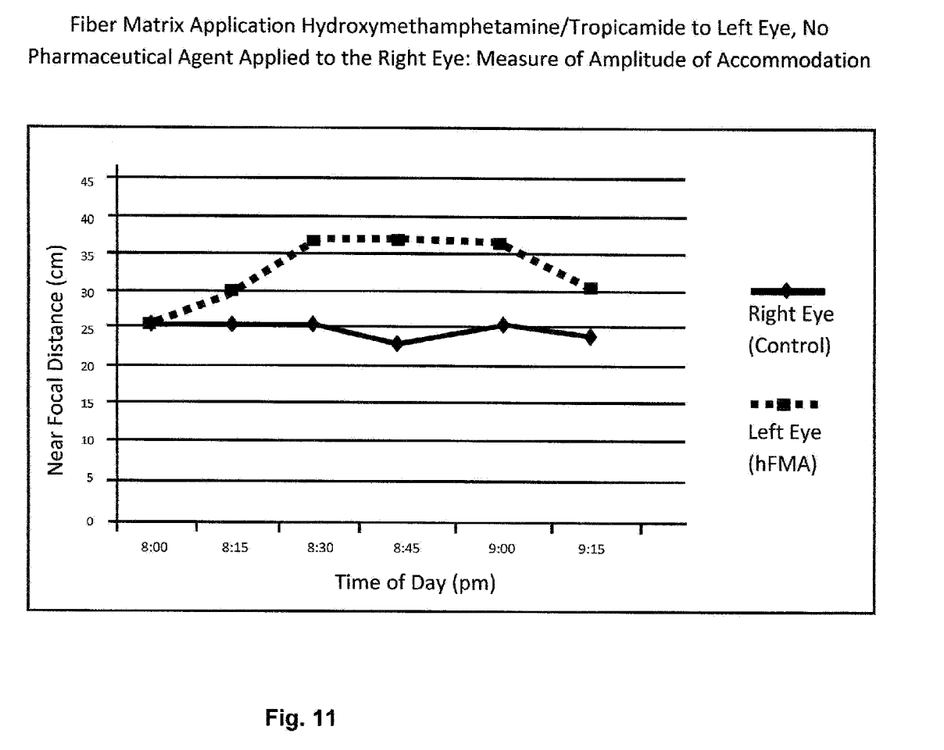
FIG. 11 illustrates the experiment using an antimuscurinic treated FMA to demonstrate the effect upon accommodation.

Referring to FIG. 11, there is shown the results of the experiment measuring the amplitude of accommodation using hydroxyamphetamine/tropicamide. The method of impregnation of the filter matrix applicator (FMA) was via solution absorption followed by air-drying at room temperature over a 3 day period. The FMA was then activated with the application of a drop of saline solution and then the FMA was subsequently applied to the left eye. The subject was a 35 year old male. It was noted that upon application of the hydroxyamphetamine/tropicamide—FMA (hFMA) to the left eye while leaving the right eye as an untreated control, that the subject experienced a 35% reduction in accommodative ability. Again, the subject reported no burning upon installation, which is usually noted with standard hydroxyamphetamine/tropicamide eye dropper bottle installation. However, gradual onset of low grade burning was noted within 1 minute of application using the FMA, but the burning was significantly less and of shorter duration than with hydroxyamphetamine/tropicamide using a conventional eye dropper bottle.

Figure 12:
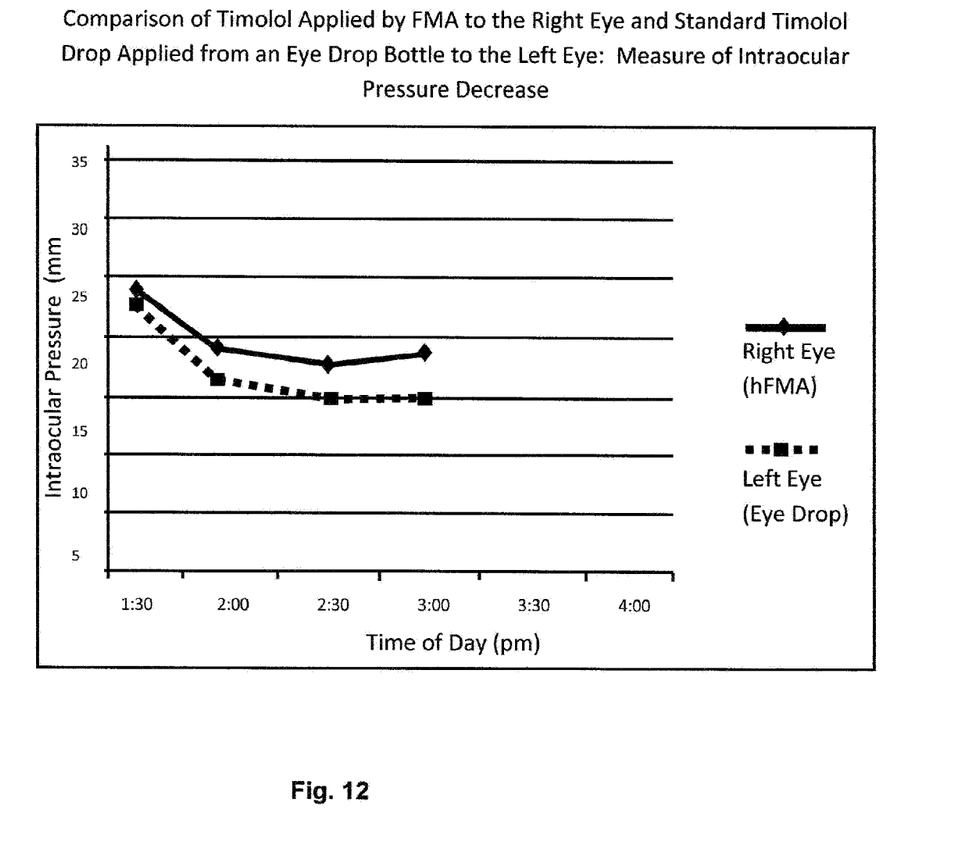
FIG. 12 illustrates the experiment using an ocular hypotensive treated FMA to demonstrate the efficacy in lowering intraocular pressure as compared to a standard ocular hypotensive eye drop.

Referring to FIG. 12, there is shown the results of the experiment using timolol. The method of impregnation of the filter matrix applicator (tFMA) was via solution absorption followed by air-drying at room temperature for a 24 hour period. The timolol—FMA (tFMA) was then activated with the application of saline solution and subsequently applied to the right eye. One eye drop of timolol from an eye dropper bottle was instilled in the left eye. The results were subsequently monitored and compared.

The FMA was easily self-applied by the patient in less than 2 seconds using a mirror. The subject reported no burning upon installation nor was there ocular irritation. In addition, no conjuctival or corneal staining was noted in the right eye. However, the subject reported significant and sustained irritation (grade 5 out of 10) of the left eye. In addition, there was mild corneal staining noted along with subsequent nasal conjunctival staining with grade 1 hyperemia upon eye drop instillation from the eye dropper bottle. The corneal staining and hyperemia persisted over a 24 hour period (in the left eye), while there continued to be no complaint about the right eye. Subject refused further testing from the eye dropper bottle of timolol due to the discomfort. A sizable reduction in intraocular pressure (IOP) was noted using both methods (nearly 30% reduction in the right eye and 35% reduction in the left eye). It should be noted that due to the impregnation technique, the tFMA contained approximately ⅓ of the volume of 1 standard eye drop (therefore it is assumed that the tFMA contained only ⅓ of the active ingredient of timolol, yet still attained a robust IOP reduction). This demonstrates similar efficacy at a significantly lower dose—which is closer to the minimum effective dose (MED) required to achieve the targeted IOP reduction (lowering the amount of active and inactive ingredients and preservatives to achieve the desired effect). The subject was a 65 year old male.

Figure 13:
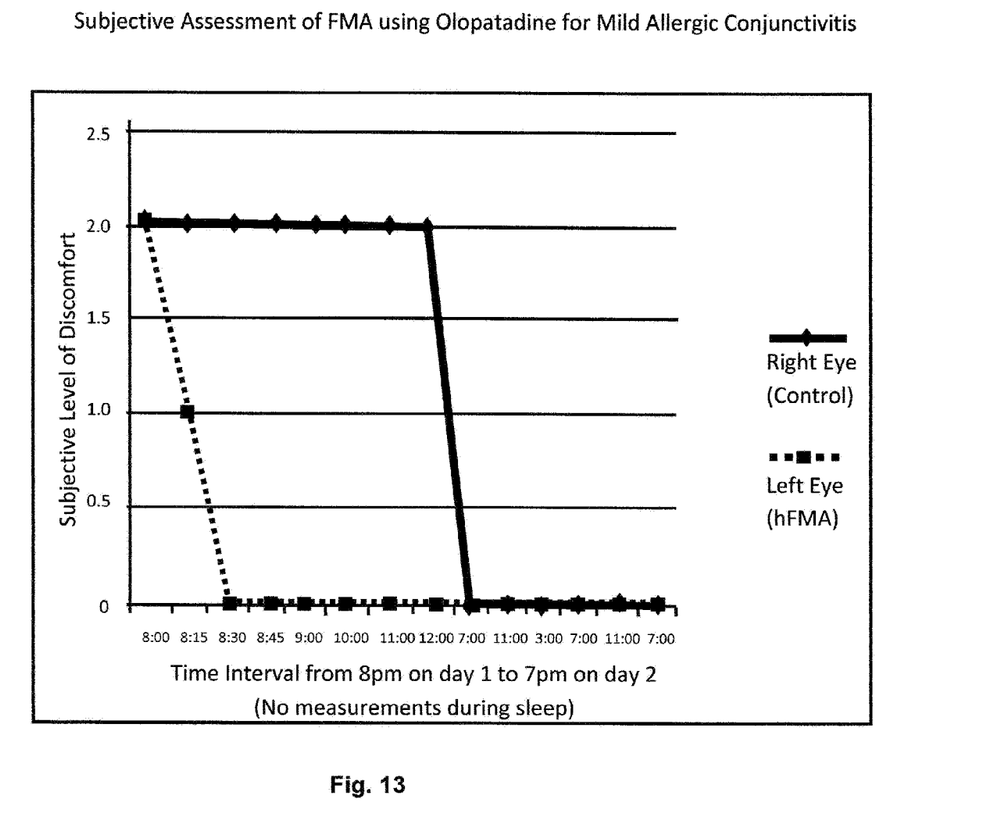
FIG. 13 illustrates the experiment using an olopatadine treated FMA to treat ocular allergy.

Referring FIG. 13, there is shown the results of the experiment using olopatadine. The method of impregnation of the filter matrix applicator (FMA) was via solution absorption followed by air-drying at room temperature for a 24 hour period. The olopatadine—FMA (oFMA) was then activated with the application of saline solution and subsequently applied to the left eye. It was noted that upon application of oFMA to the left eye while leaving the right eye as an untreated control, that the subject experienced a substantial and sustained comfort over a 24 hour period in the left eye. The FMA was applied easily in less than 2 seconds using a mirror (as the oFMA was self-applied). There was no report of burning upon instillation nor was ocular irritation noted. In addition, no conjunctival or corneal staining was noted in the left eye. The right eye remained untreated for the duration of day 1. On day 2, one olopatadine eye drop from a bottle was instilled in the right eye due to the subject's request to relieve allergic conjunctivitis symptoms—after which, relief was quickly achieved at a rate similar to that of oFMA. Although no subsequent conjunctival redness, staining, nor corneal staining was noted for the right eye, significant difficulty with instillation was observed. It took the subject several attempts before 1 drop was successful instilled into the subject's right eye.

In conclusion, the foregoing experiments show that the method of the present invention provides an easy, safe, sanitary, comfortable, and effective delivery of ocular pharmaceuticals to the eye. It greatly reduces the physical and psychological difficulties associated with eye drop instillation via standard eye drop bottles and tubes. As stated before, the medicated FMA and un-medicated FMA have a vast range of applications ranging from primary uses for eye medicine instillation for the individual patient, to installation of eye medication by a caregiver in a private or institutional setting, to the application and instillation of diagnostic eye pharmaceuticals and agents by healthcare practitioners, even to the instillation of ophthalmic mediations to veterinary patients. Patient, caregiver, and healthcare practioner preference will result in improved compliance and reduced side effects. Previous systems have been mainly paper fiber based. In addition, they were mainly used for the delivery of dyes into the eye for diagnostic purposes. If they were impregnated with medication, the amount of medication precipitated out into a drop was variable due to loss through the fibered strip over a period of time of saturation. The medicated FMA addresses this issue with the addition of a variable/adjustable absorptive filter matrix and a semi-permeable to impermeable waterproof membrane. This allows the filter matrix to hold the medication in a given area until it is precipitated out to the eye by applying a water-based solution (saline) over that same given area. Thus the FMA would then deliver a consistent and precise dose to the eye. The ability to have increased accuracy of dose and drug concentration decreases wasteful drop application and increases drug efficacy. This method can be easily adapted to replace most eye dropper bottle systems.

REFERENCES (1) S Dinslage, M Diestellhorst, A Weichselbaum, R Swerkrup. British Journal of Ophthalmology 2002; 86 1114-1117 doi 10.11362 BJO.86.10.114
(2) Abdul-Fattah A M, Bhargawa H N, Korb D R, Glonek T, Finnemore V M, Greiner J V, Optom Vis Sci 2002 July; 79(7): 435-8 (3), (4), (7) A Lux, S Maier, S Dinslage, R Suverkrup, M Deistelhorst, British Journal of Ophthalmology 2003; 87 436-440 doi 10.11436/bjo.87.4.436
(5), (6) Basics of Ocular Drug Delivery Systems. International Journal of Research in Pharmaceutical and Biomedical Sciences. ISSN:2229-3701

What is claimed is:

1. A hand-held ophthalmic applicator device for delivery of a precise amount of a dose of an ocular agent to the conjunctiva of an eye via capillary action, the device comprising: an elongated thin slender flexible handle to be hand-held for applying the dose of the ocular agent to the conjunctiva having a proximal end and an opposite distal end with a predetermined width, a predetermined length and a predetermined depth, a filter matrix element inseparably attached to the proximal end with a predetermined surface area forming a structure therein; the filter matrix element being made of a plurality of insoluble interwoven fibers of material forming a depth for the structure to contain the precise amount of the dose of ocular agent; a waterproof barrier membrane disposed between the proximal end of the handle and a first end of the filter matrix element defining the structure of the filter matrix element and forming a barrier wherein the precise dose of the ocular agent is trapped therein; a solution of the dose is formed trapped within the structure of the filter matrix element and is entrapped within the insoluble interwoven fibers of the filter matrix element adjacent the waterproof barrier membrane; wherein the ocular agent is impregnated into the filter matrix element, the filter matrix element is designed with modifiable levels of absorption and saturation according to the ocular agent being delivered and wherein the waterproof barrier membrane and the handle are affixed forming a one-piece applicator device and the precise amount of the ocular agent capable of being transferred into the conjunctiva of the eye.

2. The device of claim 1 wherein the filter matrix element is impregnated between the plurality of insoluble interwoven fibers of the filter matrix element with a medicated dose of the ocular agent that is pulverized in a granular form.

3. The device of claim 1 wherein the barrier membrane is made of an impermeable material.

4. The device of claim 1 wherein the barrier membrane is made of a semi-permeable material.

5. The device of claim 1 wherein the barrier membrane extends the predetermined width of the handle at the first end disposed between the filter matrix element and the elongated handle.

6. The device of claim 1 wherein the plurality of insoluble fibers of the filter matrix element is made of an absorbent material.

7. The device of claim 1 wherein the plurality of insoluble fibers of the filter matrix element is made of a non-absorbent material.

8. The device of claim 1 where in the plurality of fibers are made of a blend of materials relative to the precise dose of the ocular agent to be captured and released.

9. The device of claim 1 wherein the barrier membrane extends from the first end to the opposing end of the handle.

10. The device of claim 1 wherein the elongated handle having a length of 2 inches and a width of 0.25 inch.

11. The device of claim 1 wherein the surface area size varies based upon the plurality of interwoven insoluble fibers used in conjunction with the ocular agent.

12. The device of claim 1 wherein the filter matrix element is impregnated between the plurality of interwoven strands of the filter matrix element with a medicated dose of the ocular agent that is previously soaked with a medicated dose of the ocular agent and then freeze dried therein.

13. The device of claim 1 wherein the filter matrix element is saturated with a medicated dose of the ocular agent and then air dried therein.

14. The device of claim 1 wherein the filter matrix having a shape from the group consisting of cylindrical, polygonal, circular, oval, and elliptical.

15. The device of the elongated handle being made of a material from the group consisting of paper or plastic.

16. The device of the filter matrix element being made of an insoluble material from the group consisting of cotton, rayon, silk, nylon, and plastic fiber.

17. A method of applying the device of claim 1 to a conjunctiva of an eye, the method comprising:
- placing a non-irritant sterile fluid onto the filter matrix element wherein the precise dosage of the ocular agent is captured within the filter matrix element;
- moving the head forward;
- pulling the lower eyelid downward wherein the conjunctiva of the eye is exposed; and
- placing the filter matrix element in contact with the conjunctiva of the eye within a few seconds.

* * * * *